United States Patent [19]

Cannon

[11] 4,300,552
[45] Nov. 17, 1981

[54] APPARATUS FOR CONTROLLING THE FLOW OF INTRAVENOUS FLUID TO A PATIENT

[75] Inventor: Raymond E. Cannon, San Diego, Calif.

[73] Assignee: Imed Corporation, San Diego, Calif.

[21] Appl. No.: 137,557

[22] Filed: Apr. 4, 1980

Related U.S. Application Data

[63] Continuation-in-part of Ser. No. 938,910, Sep. 1, 1978, abandoned.

[51] Int. Cl.$^3$ .............................................. A61M 5/00
[52] U.S. Cl. ............................ 128/214 E; 128/214 F; 128/214 C; 128/214 R; 138/43; 138/45; 138/46; 251/4; 137/513.5
[58] Field of Search ........... 128/214 R, 214 E, 214 F, 128/214 C; 251/4; 137/513.5; 138/43.4, 43, 45, 46

[56] References Cited

U.S. PATENT DOCUMENTS

| | | | |
|---|---|---|---|
| 2,791,239 | 5/1957 | Mason | 138/45 |
| 3,144,879 | 8/1964 | Baumann | 138/43 |
| 3,429,549 | 2/1969 | Swanson | 128/214 R |
| 3,512,748 | 5/1970 | Wilson | 128/214 R |
| 3,562,782 | 2/1971 | Zychol | 138/43 |
| 3,642,026 | 2/1972 | Sielaff | 138/46 |
| 3,931,830 | 1/1976 | Gritz | 137/513.5 |
| 4,011,893 | 3/1977 | Bentley | 138/43 |
| 4,023,594 | 5/1977 | Kats et al. | 138/43 |
| 4,105,162 | 8/1978 | Drori | 138/43 |
| 4,196,753 | 4/1980 | Hammarstedt | 138/43 |

Primary Examiner—Henry K. Artis
Attorney, Agent, or Firm—Ellsworth R. Roston; Charles H. Schwartz

[57] ABSTRACT

Apparatus is included in a system for controlling the flow of intravenous fluid from a source to a patient. Such apparatus is manually adjustable to vary the rate of such fluid flow. Desired rates of fluid flow may also be set in such system when the apparatus is included in the system. The system then overrides any previous manual adjustment of such apparatus and adjusts the rate of fluid flow in accordance with any such setting. When a desired rate of fluid flow has been preset into the system, the system then operates to adjust the rate of fluid flow in an instantaneous basis so that the desired rate of fluid flow maintained.

The apparatus is removably disposed in the system for controlling the flow of fluid to the patient. Even after the adjustment by the system of the rate of fluid flow in accordance with any setting, the apparatus may be removed from the system to provide a rate of fluid flow in accordance with the manual adjustment of the apparatus.

A plug member in the apparatus defines a passage communicating at a first position with an inlet line and, at a displaced position in a particular direction, with an outlet line. A resilient member such as a diaphragm may be disposed in the particular direction in the passage and may be displaced in a transverse direction from the inlet and outlet lines. A rod constrains the diaphragm in the transverse direction.

52 Claims, 18 Drawing Figures

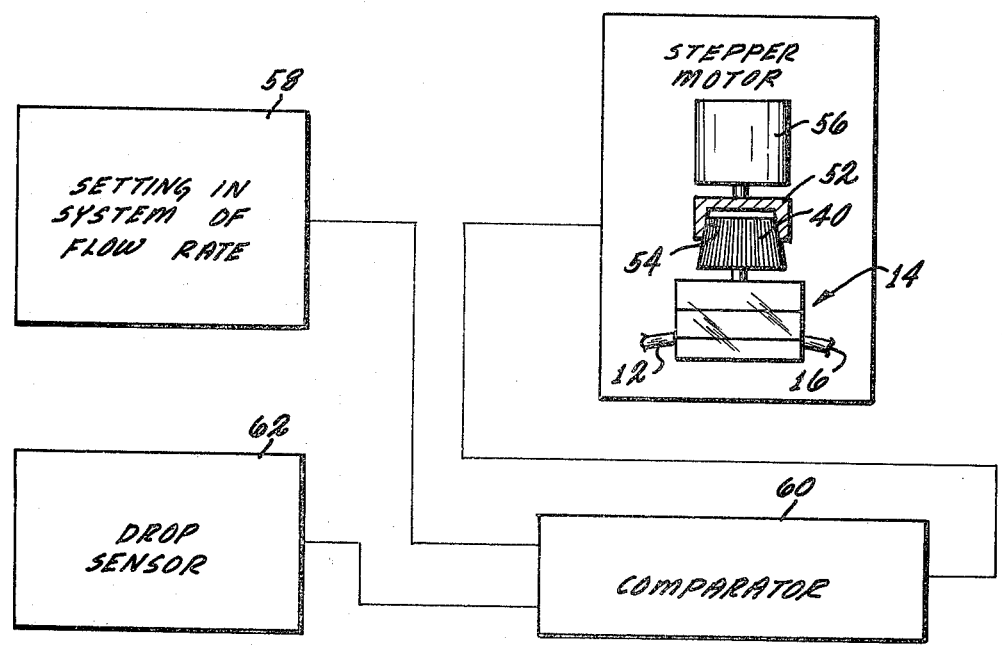
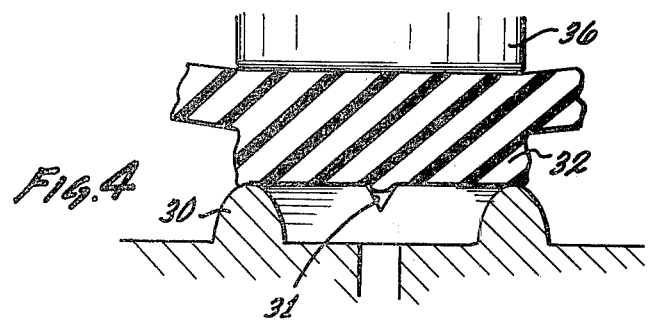
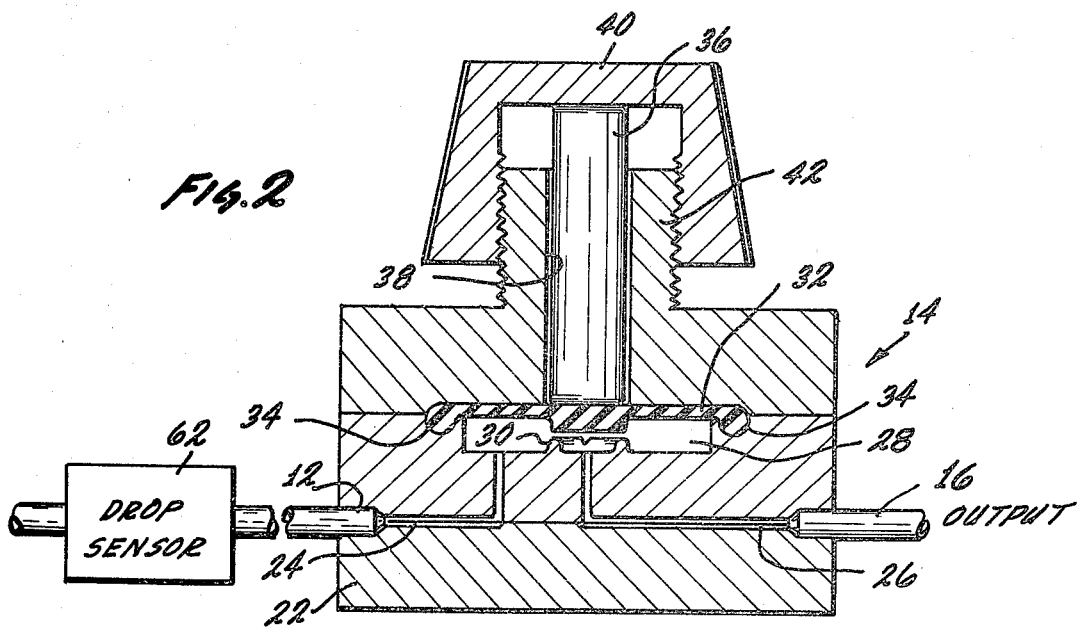

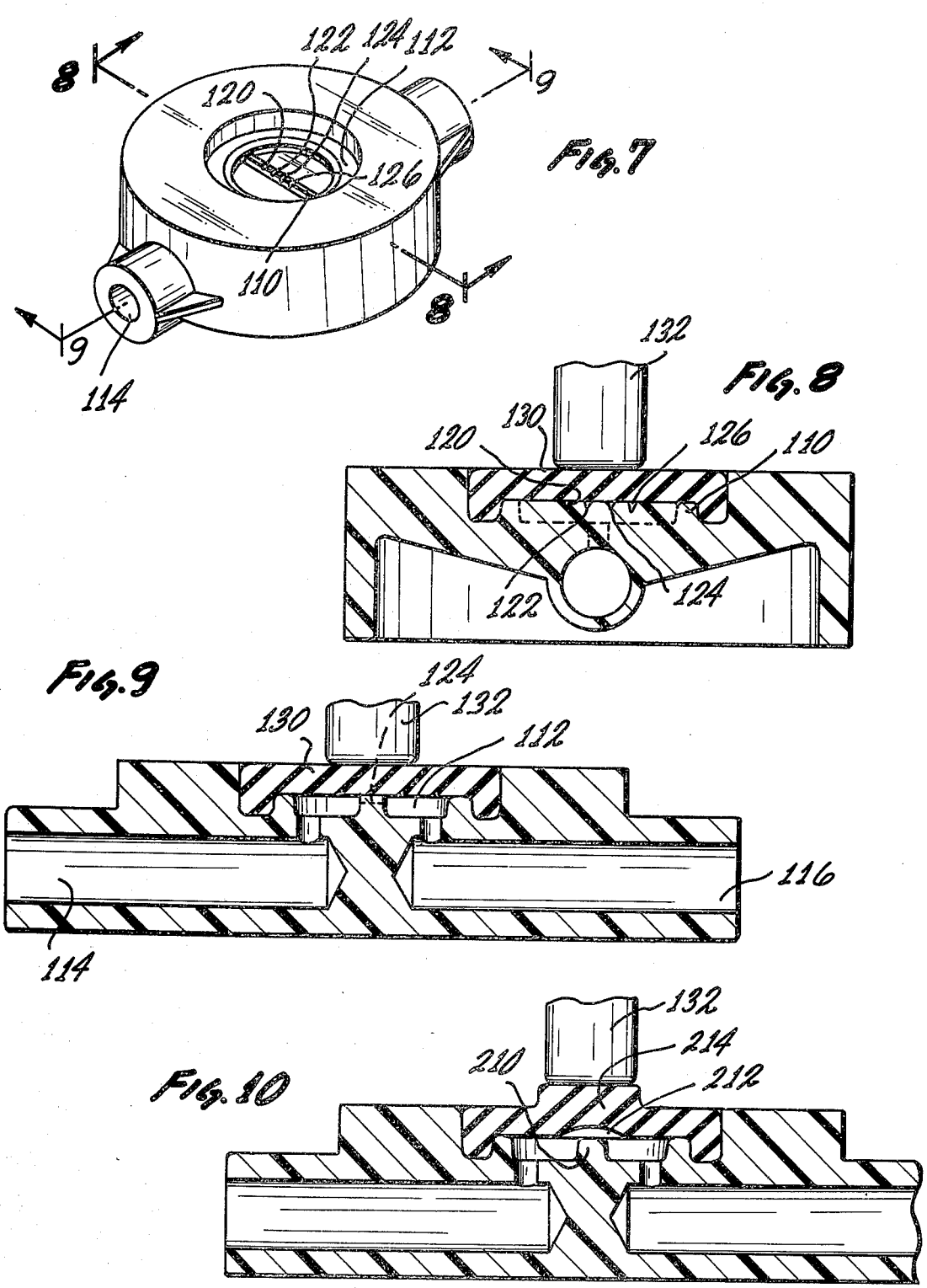

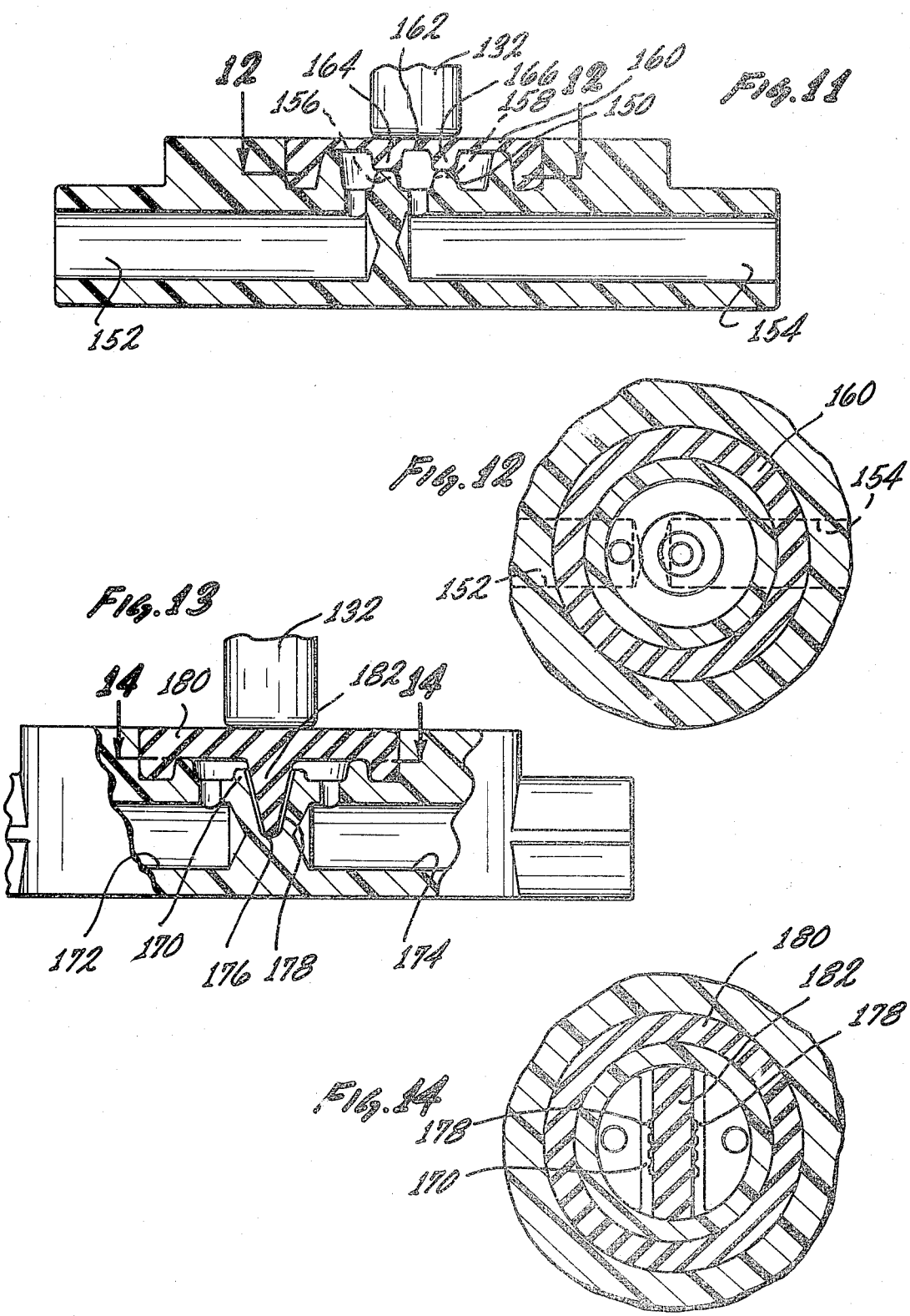

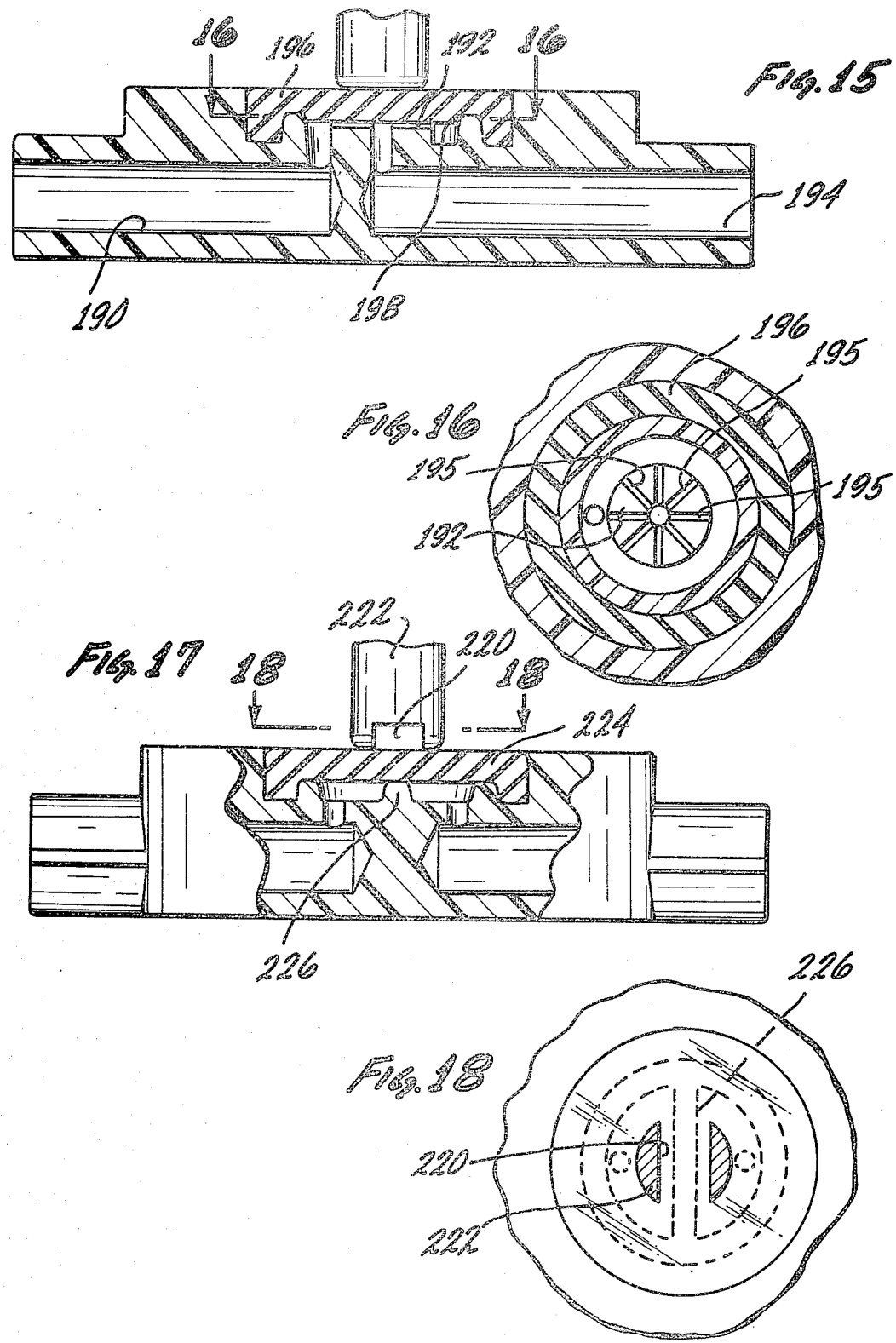

APPARATUS FOR CONTROLLING THE FLOW OF INTRAVENOUS FLUID TO A PATIENT

This application is a continuation-in-part of application Ser. No. 938,910 filed by me on Sept. 1, 1978, now abandoned and assigned of record to the assignee of record of this application.

This invention relates to removable apparatus for controlling the flow of intravenous fluid from a source to a patient. The invention particularly relates to apparatus for providing for precise controls over the rate of fluid flow to a patient during the operation of the apparatus under normal circumstances such as in the room assigned to the patient and for controls over the rate of fluid flow in accordance with manual adjustments during such abnormal conditions as the transport of a patient from one room to another. More particularly, the invention relates to apparatus for providing for a manual control over the rate of fluid flow to a patient when removed from a system, for a setting of rate in a system upon insertion of the apparatus into the system and an overriding of the manual control by the system setting under such circumstances and for the reassertion of the manual control upon a removal of such apparatus from the system.

As the practice of medicine becomes increasingly complex and increasingly refined, the equipment and techniques used to provide care for a patient have become increasingly sensitive in order to assure that the patient receives optimum care. For example, after an operation has been performed on a patient and the patient is in the recuperative state, intravenous fluid often has to be introduced to the patient. The rate of introduction of fluid to the patient is dependent upon a number of different factors including the weight, age, sex and physical state of the patient. As the patient recovers from his illness, the rate of introduction of the intravenous fluid to the patient is preferably adjusted to assure that the patient receives an optimum benefit from the fluid.

A considerable effort has been devoted over a substantial period of time to provide a satisfactory system for controlling the rate at which fluid such as intravenous fluid is introduced to a patient. Considerable progress has been made in developing a satisfactory system for certain types of operations. For example, a system providing for the pumping of fluid on a precise volumetric basis to a patient has been disclosed and claimed in Pat. No. 3,985,133 issued on Oct. 12, 1976, and assigned of record to the assignee of record of this application.

A number of fundamental problems have remained until fairly recently in systems providing for the flow of fluid on a gravitational basis to a patient. Such problems have existed until recently even though a considerable effort has been devoted to the solution of such problems. For example, a satisfactory system has not existed until recently for providing for the introduction of fluid to a patient on a gravitational basis at a precise and predetermined rate. Furthermore, a system has not existed until recently which could be used on a sterile and hygienic basis for different patients such that any contamination from the use of the system for one patient would not affect the health or safety of subsequent patients.

Applications have been recently filed which disclose and claim systems for overcoming the above difficulties. For example, application Ser. No. 913,294 has been recently filed by Jon A. Jenkins on June 7, 1978, and has been assigned of record to the assignee of record of this application. This application discloses and claims a system for providing for the flow of intravenous fluid to patient on a gravitational basis at a precise and predetermined rate and for providing a sterile and hygienic operation for individual patients.

Application Ser. No. 913,282 has also been filed by me on June 7, 1978, for a "Cassette for Intravenous Controller" and has been assigned by me of record to the assignee of record of this application. This application discloses and claims a casette which is disposed in the system to provide for the flow of fluid on the controlled basis to the patient and which is easily removable from the system so that a sterile cassette can be replaced in the system for a previously used cassette every time that the system is to be used for a different patient.

Although the system and cassette disclosed and claimed in the application specified in the previous paragraph provide for the flow of fluid on a gravitational basis to a patient at precise rates under sterile conditions, improvements would be still desirable to enhance the scope of operation of the system. For example, it would be desirable to provide a system which could be coupled to a patient even during movement of the patient and which would provide for a flow of fluid to the patient at controlled rates during such movement. In this way, intravenous fluid could be introduced to the patient at such controlled rates even during the movement of the patient from an operating room to a recovery room or from the recovery room to a room of permanent assignment in a hospital. It would also be desirable to provide such a system with instantaneous capabilities of controlling precisely and automatically the flow of fluid on a gravitational basis to the patient after the movement of the patient to a room of permanent assignment. As will be seen, a system of such capabilities would have a considerable flexibility in operation since it would provide for a controllable flow of fluid to a patient under all conditions which may be encountered in a hospital.

This application provides a system with the capabilities discussed in the previous paragraph. The system includes apparatus which is free-standing and which is manually adjustable at such times to vary the rate at which intravenous fluid flows to a patient. Such manual adjustments may be operative to control the rate of fluid flow during the time that a patient is being moved from an operating room to a recovery room or from the recovery room to his assigned room.

The apparatus may also be inserted easily and conveniently into a system when the patient is recuperating in his assigned room. At such times, desired rates of fluid flow may be set in such system, which then overrides any previous manual adjustment of such apparatus and adjusts the rate of fluid flow in accordance with any such setting. This provides for a precise control of the flow of fluid in accordance with such settings during the time that the patient is in his assigned room.

In this way, the precise controls can become operative when the patient has been moved to his assigned room and the system is operative on a semipermanent basis in the assigned room. When a desired rate of fluid flow has been preset into the system, the system then operates in a servo loop to adjust the rate of fluid flow on an instantaneous basis so that the desired rate of fluid flow is precisely maintained.

The apparatus is removably disposed in the system for controlling the flow of fluid to the patient. As a result, the manual adjustment may be provided when the apparatus is removed from the system and the system control of the rate of fluid flow may be provided when the apparatus has been coupled into the system. The removal of the apparatus from the system or the coupling of the apparatus into the system may be provided easily on an instantaneous basis.

The apparatus includes a plug member defining a passage which communicates at a first position with an input or inlet line and, at a displaced position in a particular direction, with an output or outlet line. A resilient member such as a diaphragm may be disposed in the particular direction in the passage and may be displaced in a transverse direction from the inlet and outlet lines. A rod may extend into the passage to constrain the diaphragm in the transverse direction. A button may be disposed between the inlet and outlet lines to cooperate with the diaphragm in providing a barrier against the flow of fluid through the passage between the inlet and outlet lines in accordance with the stretching of the diaphragm in the transverse direction. A knob may be adjustably threaded on the plug member to press the rod against the diaphragm.

One of the button, the diaphragm or the rod may have a channel to facilitate the flow of fluid through the passage at the desired rate. In a preferred embodiment, the buttom may be disposed laterally across the passage at a position between the inlet and outlet lines and at least two channels may be disposed in the button. Each of the channels may be provided with a different cross-sectional area than the other channels. Individual ones of the channels are progressively closed as the knob is progressively rotated in a direction to increase the force of the rod on the diaphragm.

The knob may be manually adjusted, during the movement of the patient from the operating room to the recovery room or from the recovery room to his assigned room, to control the rate at which fluid flows to the patient. The knob may be coupled to a driving member when the apparatus is inserted into the system. At such times, a motor drives the driving member through an angle dependent upon a rate which is preset into the system. In this way, the diaphragm is constrained, such as by compression, in the transverse direction in accordance with the operation of the motor. The motor may be servo-controlled to adjust the constraint of the diaphragm at each instant in the transverse direction in accordance with the rate at which drops of the fluid are actually flowing to the patient. This servo-control insures that the actual rate of flow of fluid to the patient corresponds to the rate preset into the system when the apparatus is inserted into the system.

In another embodiment, the button may be in the form of a closed loop enveloping one of the inlet and outlet lines. A channel or notch may be provided in the button at a position between the inlet and outlet lines. In still other embodiments, the channel may be provided in the diaphragm, preferably at the surface facing the notch. In other embodiments, the channel may be provided in the rod, preferably at the surface facing the diaphragm.

The apparatus included in this invention is adapted to be used in the system disclosed and claimed in copending application Ser. No. 913,294. It is also adapted to be included in the cassette disclosed and claimed in application Ser. No. 913,282 or to be used as a separate item in the system without including the casette in the system.

IN THE DRAWINGS:

FIG. 1 is a schematic diagram, partly in block form, of a system for controlling the flow of intravenous fluid to a patient on a gravitational basis;

FIG. 2 is a sectional view of control apparatus, including a cassette, capable of being included in the system of FIG. 1 and shows the positioning relative to such control apparatus of a drop sensor included in the system shown in FIG. 1;

FIG. 4 is an enlarged fragmentary sectional view of certain elements of the cassette shown in FIGS. 2 and 3;

FIG. 7 is a perspective view of a preferred embodiment of a cassette for use in the apparatus shown in FIGS. 1, 5 and 6;

FIG. 8 is a fragmentary sectional view of the cassette shown in FIG. 6 and is taken substantially on the line 8—8 of FIG. 7;

FIG. 9 is a fragmentary sectional view of the cassette shown in FIGS. 7 and 8 and is taken substantially on the line 9—9 of FIG. 7;

FIG. 10 is a fragmentary sectional view of another embodiment of a cassette for use in the apparatus in FIGS. 1, 5 and 6;

FIG. 11 is a fragmentary sectional view of another embodiment of a cassette for use in the apparatus of FIGS. 1, 5 and 6;

FIG. 12 is an enlarged fragmentary sectional view of certain elements of the cassette shown in FIG. 11 and is taken substantially on the line 12—12 of FIG. 11;

FIG. 13 is a fragmentary sectional view of a further embodiment of a cassette for use in the apparatus of FIGS. 1, 5 and 6;

FIG. 14 is an enlarged fragmentary sectional view of certain elements of the cassette shown in FIG. 13 and is taken substantially on the line 14—14 of FIG. 13;

FIG. 15 is a fragmentary sectional view of a still further embodiment of a cassette for use in the apparatus shown in FIGS. 1, 5 and 6;

FIG. 16 is an enlarged fragmentary sectional view of certain elements of the cassette shown in FIG. 15 and is taken substantially on the line 16—16 of FIG. 15;

FIG. 17 is a fragmentary sectional view of still another embodiment of a cassette for use in the apparatus shown in FIGS. 1, 5 and 6; and FIG. 18 is an enlarged fragmentary sectional view of certain elements of the cassette shown in FIG. 17 and is taken substantially on the line 18—18 of FIG. 17.

Figure 3:
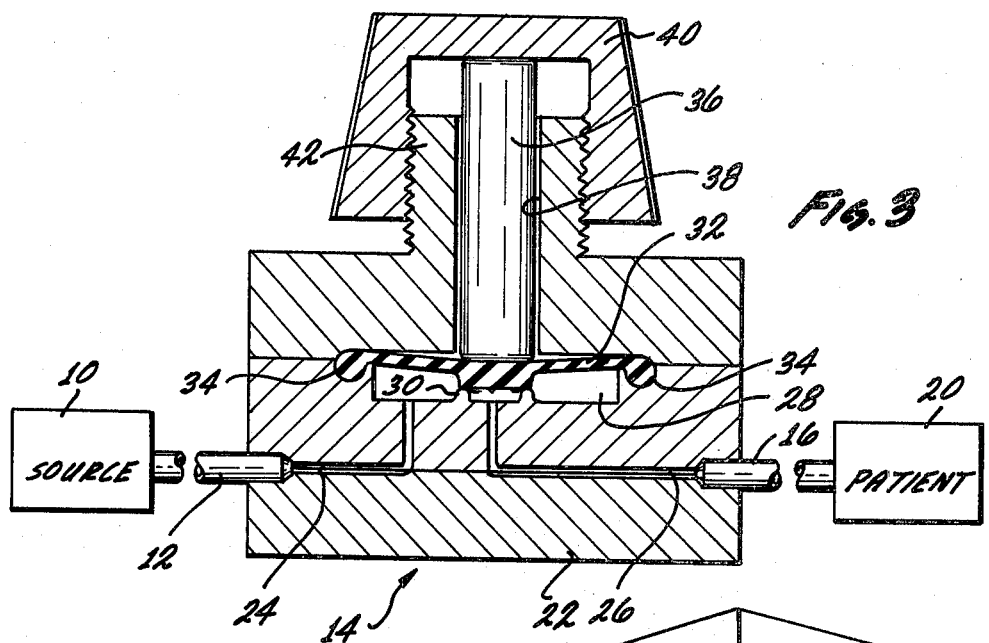
FIG. 3 is a sectional view of the apparatus, including the cassette, shown in FIG. 2 when the apparatus is removed from the system shown in FIG. 1 and is in a position to provide for the flow of fluid at a very low rate.

FIG. 3 illustrates equipment which forms a part of this invention and which provides for a flow of intravenous fluid to a patient at a rate dependent upon a manual adjustment of such apparatus. The equipment includes a source 10 of intravenous fluid and a conduit 12 extending from such source to apparatus generally indicated at 14 and forming a part of this invention and constituting a cassette. An output conduit 16 extends from the apparatus 14 to a patient schematically illustrated at 20.

The apparatus 14 includes a plug member 22 formed from a suitable material such as a plastic material. The plug member 22 is provided with an input line 24 constructed to receive the input conduit 12 and with an output line 26 constructed to receive the output conduit 16. A cavity or passage 28 is disposed between, and in communication with, the input line 24 and the output line 26. Button 30 is disposed in the passage 28 in a closed loop around one of the lines such as the output line 26 and is preferably provided with an annular configuration. The button 30 is preferably provided with a channel or notch at one position as at 31 (FIG. 4) to facilitate the flow of fluid on a controlled basis. The notch 31 may be V-shaped to provide a progressive control over the rate of fluid flow.

A resilient member such as a diaphragm 32 is disposed in the cavity or passage 28. The ends of the diaphragm 32 are provided with a bulbous construction and the bulbous ends are disposed in sockets 34 in the plug member 22 to maintain the diaphragm in a taut relationship. The diaphragm 32 is disposed so that it extends in the same direction as the distance between the input line 24 and the output line 26 at the positions at which these lines communicate with the passage 22.

A pusher rod 36 is disposed in a socket 38 in the plug member 22. The pusher rod 36 is disposed against the diaphragm 32 at a position intermediate the sockets 34 to stretch the diaphragm in a direction transverse to the disposition of the diaphragm in the passage 22. A knob 40 is internally threaded on a threaded protuberance 42 extending from the plug member 22. The knob 40 presses against the pusher rod 36. The knob 40 may be provided with a frusto-concial external surface which may be knurled or otherwise deformed to facilitate gripping.

The knob 40 may be rotatably adjusted on the protuberance 42 to adjust the pressure exerted against the pusher rod 36. This in turn provides for an adjustment of the force exerted by the pusher rod 36 against the diaphragm 32. In this way, the position of the diaphragm 32 adjacent the button 30 may be adjusted in accordance with adjustments in the positioning of the knob 40 so as to control the rate at which fluid flows through the passage 28 from the input line 24 to the output line 26. The manual adjustment of the knob 40 accordingly provides for a control of the rate at which fluid flows from the source 10 to the patient 20.

The channel or notch 31 is provided in the button 30 to obtain a flow of fluid to the patient at low rates in accordance with the adjustment of the knob 40. This may be seen on a schematic basis in FIG. 4. At such low rates, the diaphragm 32 tends to be drawn into the notch 31. The positioning of the diaphragm 32 in the notch 31 is dependent upon the adjustment of the knob 40. As a result, for low settings of the knob 40, fluid can flow through the passage to the output line only in the space between the diaphragm 32 and the bottom of the V-shaped notch 31.

The apparatus disclosed above is adapted to be used when the patient is being moved from an operating room to a recovery room or from a recovery room to an assigned room. Since the apparatus 14 is relatively small and can even be held in the palm of a hand, it can be held by a nurse or even can be disposed in the palm of a patient as the patient is being moved from one room to another. During such movement, the rate of flow of fluid to the patient can be controlled by the adjustment of the knob 40 on the protuberance 42.

FIG. 1 illustrates a system for providing an automatic control over the rate of flow of fluid on a gravitational basis to a patient. The system includes the apparatus 14 shown in FIGS. 2 and 3 and described in detail above. The apparatus 14 is adapted to be supported in fixed position relative to such system by a housing generally indicated at 50 in FIG. 5. The holder includes a drive member 52 (FIG. 5) which is provided with a socket 64. The socket 54 is knurled or otherwise deformed in a manner similar to the external surface of the knob 40 so as to engage the knob and rotate the knob as it rotates. The drive member 52 may be spring loaded to facilitate the driving relationship between it and the knob 40. The drive member 52 is adapted to be driven by a stepper motor 56.

The stepper motor 56 is included in an electrical system which is shown on a schematic basis in FIG. 1. The system includes settings 58 (FIG. 5) which are disposed on the front panel of the housing 50 and which are preferably provided with digital capabilities of a plurality of digits of progressive value. For example, three digits may be provided to register the values of units, tens and hundreds to provide capabilities of selecting rates of digital flow between values of "1" and "999".

The selections in the settings 58 are introduced to a comparator 60 (FIG. 1) which compares such desired values with the actual values of flow provided by a drop sensor 62. The drop sensor may be of a conventional construction and is operative to sense the number of drops of fluid flowing through the output line 12 in a particular period of time such as one second. The comparator 60 compares the signals from the settings 58 and the drop sensor 62 and produces an error signal representing any differences between the characteristics of the signals being sensed. The error signal is then introduced to the stepper motor 56 to operate the stepper motor in a direction for reducing the error signal. The stepper motor drives the drive member 52, which in turn drives the knob 50, in a direction to control the flow of fluid through the passage 28. In this way, the stepper motor 56 is controlled on an instantaneous basis to obtain a flow of fluid through the output line 16 at a rate directly related to the values provided in the settings 58.

Figure 5:
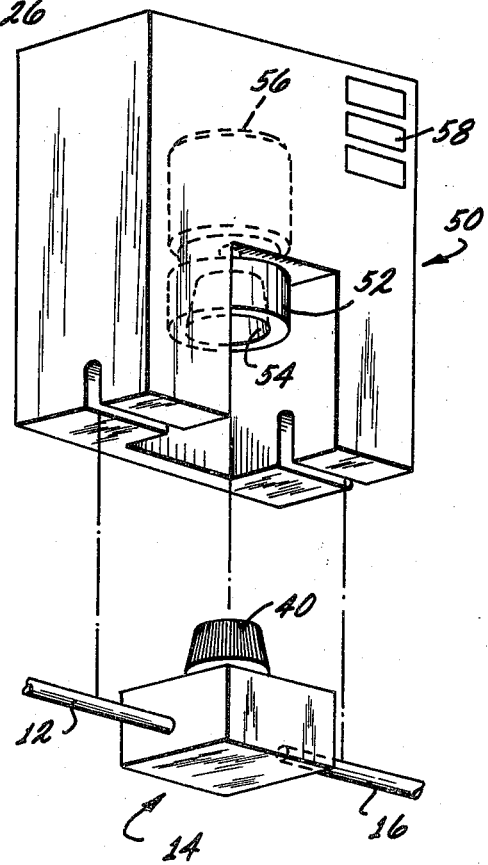
FIG. 5 is an exploded perspective view of the system shown in FIG. 1 and of the apparatus of FIGS. 2 and 3 in a position removed from the system.

As will be seen from FIG. 5, the apparatus 14 is adapted to be removably disposed in the housing 50. The housing 50 may include the drive member 52 and the stepper motor 56. In this way, the apparatus 14 may be easily coupled into the housing 50 when the system shown in FIG. 5 is to be operative in an assigned room of a patient to provide a flow of fluid to the patient at a precise rate in a closed-loop.

The apparatus 14 may be easily decoupled from the housing 50 to operate independently of the system when the patient is being moved from an operating room to a recovery room or from a recovery room to an assigned room. Under such circumstances, the manual adjustment of the knob 40 is sufficient to regulate the flow of fluid at a desired rate with sufficient accuracy in an open-loop servo so that the patient is receiving good medical attention.

The embodiment shown in FIGS. 1 through 5 and described above is practical and has been successfully tested and operates within the principles of the invention. However, this embodiment has occasionally experienced problems of hysteresis. Such hysteresis results from the failure of the diaphragm 32 to respond properly when the knob 40 is moved in a direction to relieve the force on the diaphragm. In other words, the diaphragm occasionally tends to remain in the notch 31 even though it should move from the notch as the force exerted by the rod 36 on the diaphragm is relieved. This causes fluid to flow through the passage 28 between the inlet line 24 and the outlet line 26 at a rate less than that desired. It will be appreciated that this occurs only when the knob 40 is manually adjusted since the rate of fluid flow is automatically adjusted when the rate of fluid flow is under the control of the system shown in FIGS. 1 and 5.

FIGS. 7, 8 and 9 illustrate a preferred embodiment of a disposable cassette since this embodiment overcomes any problems of hysteresis. The embodiment shown in FIGS. 7, 8 and 9 is substantially identical to the embodiment shown in FIGS. 2 and 3 except for the construction and disposition of the button. In the embodiment shown in FIGS. 7, 8 and 9, a button 110 is disposed laterally across a passage 112 at a position between an inlet line 114 and an outlet line 116 to provide a barrier against the flow of fluid through the passage between the inlet and outlet lines.

Channels such as channels 120, 122, 124 and 126 are provided in the button 110 at laterally spaced positions along the button. Although four channels are shown, any number of channels or notches equal to or greater than two may be provided. Each of the channels may be provided with an individual cross-sectional area. Preferably, each of the channels 120, 122, 124 and 126 is provided with a V-shaped cut having a different cross-sectional area than the cross-sectional area of the other channels. For example, the channels 122, 124 and 126 may respectively have a greater cross-sectional area than the channels 120, 122 and 124.

By providing a plurality of channels of individual cross-sectional areas, the different channels become sequentially closed as the force exerted on a diaphragm 130 is progressively increased. Thus, fluid tends to flow through at least the channel 126, and possibly one or more of the other channels, provided that a rod 132 has not been manually positioned to the position where the flow of fluid has been completely interrupeted. Since the fluid tends to flow through at least one of the channels and since the channels are laterally displaced, any tendency for the diaphragm 130 to remain in the compressed position across the lateral dimension represented by the different channels is minimized when the force for constraining, such as by compression, the diaphragm is relieved.

FIGS. 11 and 12 illustrate another embodiment of the invention. In this embodiment, a button 150 is disposed in a closed loop around one of an inlet line 152 and an outlet line 154. Channels or notches 156 and 158 are disposed in the button 150. The notches 156 and 158 are preferably V-shaped in cross section. A diaphragm 160 cooperates with the notches to control the flow of fluid in the notches. This cooperation is facilitated by providing a relieved portion 162 in the diaphragm at a position between the notches 156 and 158. The relieved portion 162 defines thickened portions 164 and 166 in the diaphragm 160 at positions respectively contiguous to the notches 156 and 158. The thickened portions 164 and 166, and the relieved portion between such thickened portion, cooperate with the notches in controlling the flow of fluid at the desired rate. Although the relieved portion 162 is shown and described as being included in the embodiment of FIGS. 11 and 12, it will be appreciated that the diaphragm 160 can be provided with a substantially uniform thickness.

FIGS. 13 and 14 illustrate another embodiment of the invention. In this embodiment, a button 170 is disposed between an inlet line 172 and an outlet line 174. The button is provided with a relieved portion 176 at an intermediate position along its length. A channel or notch 178 is provided along the length of the relieved portion. A diaphragm 180 is provided with a thickened portion 182 at a position corresponding to the position of the relieved portion 176. The thickened portion 182 has a configuration substantially matching that of the relieved portion 176. In this way, the thickened portion 182 cooperates with the channel 178 in controlling the rate at which fluid flows through the channel between the inlet line 172 and the outlet line 174.

In the embodiment shown in FIGS. 15 and 16, an inlet line 190 is provided at the periphery of a button 192 and an outlet line 194 is extended through the button. A plurality of channels 195 may be disposed in the button 192 in a configuration corresponding to the radial spokes of a wheel so as to communicate with the outlet line 194 at their inner end. A diaphragm 196 may be provided with a thickened portion 198 at positions adjacent the button 192.

In all of the embodiments described above, one or more channels have been provided in a button. It will be appreciated, however, that the channel may be provided in the diaphragm or in the rod without departing from the scope of the invention. For example, in the embodiment shown in FIG. 10, a button 210 may be provided without any channel and a channel 212 may be provided in a diaphragm 214 at a position adjacent the button. Furthermore, FIGS. 17 and 18 illustrate an embodiment in which a channel 220 is provided in a rod 222 at a position adjacent that in which a diaphragm 224 cooperates with a button 226.

Figure 6:
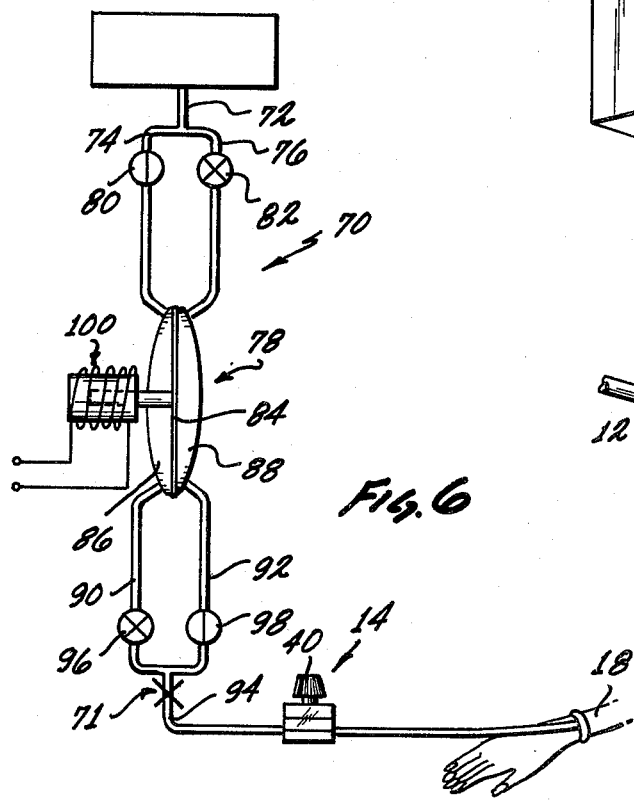
FIG. 6 is a schematic view of a cassette which may be constructed to include the apparatus of FIGS. 2 and 3.

The apparatus 14 may also be included in a cassette which is generally indicated at 70 in FIG. 6 and which is disclosed and claimed in application Ser. No. 913,282. As disclosed in such application, the cassette 70 may be included in a system, such as that shown in FIG. 1, for controlling the rate of flow of intravenous fluid to a patient on a gravitational basis. When the apparatus 14 is included in the cassette 70, it may be permanently disposed in the cassette rather than being removable as in the embodiment described above. However, even when the apparatus 14 is included in the cassette, it has the flexibility of being manually adjustable to control the rate of flow of intravenous fluid to a patient or of being controlled by the system in accordance with adjustments in the setting 58 shown in FIG. 5.

When the apparatus 14 is included in the cassette 70, it may be disposed at any convenient position in the hydraulic circuit provided by the cassette. This hydraulic circuit is shown on a schematic basis in FIG. 6. For example, the apparatus 14 may be disposed at a position 71 designated as "X" in an output line 72 in the cassette. The position "X" is provided in the output line 72 at a position effluent any branching of the fluid into auxiliary lines in the cassette. In this way, all of the fluid flowing through the cassette passes through the apparatus 14.

The hydraulic circuit shown in FIG. 6 includes a pair of auxiliary lines 74 and 76 extending from the input line 70 to opposite ends of a chamber generally indicated at 78. Valves 80 and 82 are respectively disposed in the auxiliary lines 74 and 76. A resilient member such as a diaphragm 84 is disposed in the chamber 78 to divide the chamber into a pair of compartments 86 and 88. Auxiliary lines 90 and 92 respectively extend from the compartments 86 and 88 to an output line 94. Valves 96 and 98 are respectively disposed in the auxiliary lines 90 and 92. The apparatus 14 is preferably disposed in the output line 94 as illustrated in FIG. 6.

The diaphragm 84 is constrainable, such as by compression, in the chamber 78 to increase the volume of one of the compartments and correspondingly reduce the volume of the other compartment. A transducer generally indicated at 100 is movable with the movement of the diaphragm to indicate the disposition of the diaphragm at each instant. The transducer 100 produces at each instant a signal which controls the direction in which fluid flows into and out of the chamber. For example, the valves 80 and 98 may be initially open and the valves 82 and 96 may be initially closed. In this relationship, fluid flows into the compartment 86 and out of the compartment 88 and accordingly constrains, such as by compression, the diaphragm 84 into the compartment 88. When the diaphragm has been constrained to a particular limit, the transducer 100 produces a signal which causes the valves 80 and 98 to close and the valves 82 and 96 to open. In this relationship, fluid flows into the compartment 88 and out of the compartment 86 and accordingly causes the transducer 100 to stretch into the compartment 86.

In this way, fluid flows at alternate times into the compartment 86 and out of the compartment 88 and at the other times into the compartment 88 and out of the compartment 86. The rate of fluid flow into and out of the compartments 86 and 88 is dependent upon the setting of the knob 40 in the apparatus 14. The setting of the knob 40 may be manually adjusted or the knob 40 may be automatically set by the system of FIGS. 1 and 5 in accordance with values inserted into the settings 58.

The apparatus and system described above has certain important advantages. It provides for the introduction of fluid on a gravitational basis to a patient at preset rates even when the patient is being moved from an operating room to a recovery room or from a recovery room to an assigned room. This rate of fluid flow may be manually preset to any desired value.

The apparatus and the system including the apparatus also provide for the flow of intravenous fluid on a gravitational basis to a patient at precisely controlled rates when the patient has been moved to his assigned room. Such precisely controlled rates may be inserted by a physician or nurse into the system by the operation of the setting 58. The system then operates in a closed-loop servo to insure at each instant that the rate of fluid flow to the patient is precisely regulated at the desired rate inserted by the physician or nurse.

The apparatus and system are also advantageous because they can be easily converted between manual control of the rate of fluid flow or system control of the rate of fluid flow. The apparatus and system are further advantageous because the apparatus 14 is relatively small and light and can be easily moved with the patient as the patient is transported from the operating room to the recovery room or from the recovery room to the assigned room.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination for controlling the rate of flow of fluid to a patient,
   means for providing for a source of fluid,
   means defining an inlet line from the souce and an outlet line to the patient,
   means disposed between the inlet line and the outlet line for defining a passage communicating with the inlet and outlet lines,
   resilient means defining a particular periphery of, and communicating with, the inlet and outlet lines for controlling the size of the passage in accordance with the positioning of the resilient means, and
   a button disposed in the channel between the inlet line and the outlet line,
   means adjustably positioned and coupled to the resilient means for varying the positioning of the resilient means in the passage in accordance with such adjustable positioning, to control the rate at which fluid flows through the inlet line to the outlet line,
   one of the resilient means, the button and the coupling means being provided with a channel to control the rate at which the fluid flows through the passage between the inlet and outlet lines in accordance with the variations in the positioning of the resilient means.

2. The combination set forth in claim 1 wherein the resilient means constitutes a diaphragm defining the particular periphery and the diaphragm is pressed into the passage by the adjustably positioned means to control the size of the passage in accordance with such pressure.

3. The combination set forth in claim 1 wherein
   the adjustably positioned means are manually adjustable and
   means are included in the adjustably positioned means for adjustably setting the flow of fluid to any value desired and
   means are responsive to the adjustable setting of the desired flow of fluid for adjusting the positioning of the adjustably positioned means in accordance with such setting.

4. The combination set forth in claim 2 wherein
   the adjustably positioned means constrains the diaphragm into the passage in accordance with the adjustments in the position of the adjustably positioned means and the channel is disposed in the button.

5. The combination set forth in claim 4 wherein the button is provided with a channel in at least one position and wherein the diaphragm is positioned to be constrained into the channel in accordance with the positioning of the adjustably positioned means to facilitate the flow of fluid through the passage and the inlet and outlet lines at the controlled rate.

6. The combination set forth in claim 2 wherein the button is provided with at least a pair of channels and the channels are provided with different sizes to become closed at progressive times as the diaphragm is progressively constrained and to become opened in a reverse relationship at progressive times as the constraint on the diaphragm is progressively released.

7. The combination set forth in claim 6 wherein the button extends laterally across the passage and provides a barrier against the flow of fluid and wherein a plurality of channels are provided at laterally spaced positions in the button.

8. The combination set forth in claim 7 wherein each of the channels has a different cross-sectional area than the other channels.

9. The combination set forth in claim 2 wherein the channel is disposed in the diaphragm.

10. The combination set forth in claim 2 wherein the channel is disposed in the coupling means.

11. In combination for controlling the rate of flow of intravenous fluid to a patient,
first means defining an inlet line,
second means spaced from the first means and defining an outlet line,
the first and second means being spaced by a cavity, and
third means disposed in the cavity and defining a sealed passage of adjustable volume for the flow of fluid from the first means into the second means, the first means and the second means being disposed on the same side of the passage defined by the third means,
the third means including resilient means disposed in the cavity for controlling the flow of fluid through the passage in accordance with the constraint of the resilient means and further including adjustable means disposed against the resilient means to control the flow of fluid through the passage,
a button disposed in the passage to block the flow of fluid through the passage between the inlet and outlet lines, and
at least one channel in the button to cooperate with the diaphragm in providing a controlled flow of fluid between the inlet and outlet lines.

12. The combination set forth in claim 11 wherein
the resilient means includes a resilient diaphragm sealing the passage along a particular periphery and the adjustably positioned means includes a pusher rod disposed against the diaphragm at a position within the area encompassed by the button and further includes a knob pressing the pusher rod against the diaphragm and rotatable to adjust the force exerted by the pusher rod against the diaphragm.

13. The combination set forth in claim 12 wherein
the button is disposed laterally across the passage at a position between the inlet and outlet lines and a plurality of channels are disposed at laterally spaced positions along the button and each of the channels is provided with an individual cross-sectional configuration.

14. The combination set forth in claim 13 wherein
the channels are provided at the outer configuration of the button and each of the channels is provided with a different cross-sectional area than the other channels in the plurality and the diaphragm is movable into the channels to close sequentially the channels of progressively increasing cross-sectional area.

15. The combination set forth in claim 11 wherein
the button is provided with a looped configuration and is disposed around one of the inlet and outlet lines.

16. The combination set forth in claim 15 wherein
the channel is disposed in the button at a position between the inlet and outlet lines.

17. In combination for controlling the rate of flow of intravenous fluid to a patient,
a cassette,
means defining a passage in the cassette for the flow of fluid,
resilient means defining in the cassette a particular boundary of the passage for controlling the size of the passage in accordance with variations in force exerted against the resilient means,
means disposed in the cassette and defining an inlet to the passage and an outlet from the passage,
manually operable control means extending through the cassette from a position outside of the cassette into direct engagement with the resilient means for producing an adjustable force against the resilient means in a direction to limit the size of the passage in accordance with such manual operation,
a housing constructed to support the cassette,
means disposed on the housing and settable to any desired rate of fluid flow, and
means disposed in the housing and operatively coupled to the control means and to the settable means and responsive to any setting of the settable means for overriding any manual positioning of the control means to position the control means in accordance with such setting.

18. The combination set forth in claim 17 wherein
the manually adjustable means include a plug member and a know threadedly disposed on the plug member and the settable means and the overriding means are disposed in a system for providing a controlled flow of drops of the intravenous fluid to the patient at a rate dependent upon the setting of the settable means and wherein the cassette is removable from the housing to provide for the flow of fluid through the passage in accordance with the manual adjustment of the control means.

19. The combination set forth in claim 18 wherein
the resilient means are constructed to be constrained in a direction transverse to the direction of fluid flow to limit the size of the passage and wherein the passage is defined by a button blocking the passage of the fluid between the inelt and outlet lines and the button is provided with at least one channel to provide for a controlled flow of fluid.

20. The combination set forth in claim 18 wherein
the channel in the button is substantially V-shaped and the overriding means include a drive member disposed to become coupled to the control means and the control means are constructed to be driven by the drive member and the overriding means further include a motor for driving the drive member and means for controlling the operation of the motor to obtain a drive of the drive member to a position dependent upon the setting of the settable means.

21. The combination set forth in claim 20 wherein
the button extends laterally across the passage at a position between the inlet and outlet lines and a plurality of channels are provided in the button at spaced positions laterally along the button and each of the channels has an individual cross-sectional area.

22. In combination for controlling the flow of fluid from a source to a patient,
a housing,
an inlet line in the housing,
an outlet line in the housing, a cavity in the housing in communication with the inlet and outlet lines, a resilient diaphragm disposed in the cavity to define a particular boundary of a passage extending between the inlet and outlet lines, means extending into the cavity from a position external to the housing and coupled to the diaphragm to constrain the diaphragm in accordance with the operation of the coupling means, a button disposed between the inlet and outlet lines and blocking the passage against the flow of fluid between the inlet line and the outlet line, and means operably associated with a particular one of the button, the diaphragm and the coupling means and cooperating with at least another one of the button, the diaphragm and the coupling means to define a channel for a controlled flow of fluid through the inlet line, the passage and the outlet line.

23. The combination set forth in claim 22 wherein the channel is disposed in the button and wherein the coupling means constitutes a rod disposd against the diaphragm and adjustably positioned to constrain the diaphragm for controlling the size of the package.

24. The combination set forth in claim 23 wherein the button is disposed laterally across the passage and is provided with dimensions to block the flow of fluid through the passage and a plurality of chanels are provided at spaced positions laterally along the button.

25. The combination set forth in claim 24 wherein each of the channels is dimensioned to pass a different amount of fluid than the other channels and the diaphragm is progressively constrained to close sequentially the channels passing progressive amounts of fluid.

26. The combination set forth in claim 23 wherein the button is disposed in a closed loop around one of the inlet and outlet lines and the channel is provided in the bottom at a position between the inlet and outlet lines.

27. The combination set forth in claim 22 wherein the channel is disposed in the diaphragm at a position facing the button.

28. The combination set forth in claim 22 wherein the coupling means constitutes a rod disposed against the diaphragm and the channel is disposed in the rod at a position facing the diaphragm.

29. The combination set forth in claim 23 wherein a plurality of channels are provided in the button and the inlet line extends through the button and the channels have the relative configuration of spokes extending from spaced positions around the periphery of the button to one of the inlet and outlet lines and wherein the other one of the inlet and outlet lines is disposd outwardly in the passage from the button.

30. The combination set forth in claim 23 wherein a plurality of channels are provided in the button and the inlet line extends through the button and the channels have the relative configuration of spokes extending from spaced positions around the periphery of the button to the inlet line and wherein the outlet line is disposed outwardly in the passage from the button.

31. The combination set forth in claim 23 wherein the button has a recessed portion and the channel is disposed in the recessed portion of the button and the inlet and outlet lines are disposed outwardly from the button.

32. In combination for controlling the flow of fluid from a source to a patient, means providing settings of desired rates of fluid flow, means for providing for the flow of the fluid from the source to the patient, means for sensing the rate at which the fluid flows from the source to the patient, means responsive to the settings of the desired rate of fluid flow and to the sensings of the actual rate of flow fluid for producing error signals having characteristics representing any differences in the desired and actual rates, means including an adjustably positioned member for controlling the rate of flow of the fluid through the control means in accordance with the adjustable positioning of the member, means for removably receiving the control means, and means responsive to the error signal, with the control means disposed in the receiving means, for adjusting the positioning of the member to minimize the error signal.

33. The combination set forth in claim 32 wherein the control means includes a drive member for engaging the adjustably positioned member to adjust the position of the adjustably positioned member and further includes a motor responsive to the error signal for driving the drive member in a direction to minimize the error signal.

34. The combination set forth in claim 33 wherein the control means defines a passage for the flow of fluid and a resilient member is disposed in the passage for controlling the size of the passage in accordance with the constraint of the resilient member and the adjustably positioned means adjustably constrains the resilient member in the passage in accordance with adjustments in its positioning.

35. The combination set forth in claim 1 wherein the means defining the inlet and outlet lines and the passage and the adjustably positioned means are disposed in a cassette and the cassette includes the passage for receiving fluid from the inlet line and passing fluid to the outlet line and the error signal means includes transducer means for sensing the rate of flow of fluid through the passage.

36. In combination for controlling the flow of fluid from a source to a patient, means providing settings of desired rates of fluid flow, means for providing for the flow of the fluid from the source to the patient, means for sensing the rate at which the fluid flows from the source to the patient , means responsive to the settings of the desired rate of fluid flow and to the sensings of the actual rate of fluid flow for producing error signals having characteristics representing any differences in the desired and actual rates, housing means, the flow means including a cassette removably disposed in the housing means for controlling the flow of fluid from the source, means including an adjustably positioned member included in the cassette for controlling the rate of flow of the fluid through the control means and the cassette in accordance with the adjustable positioning of the member, and means responsive to the error signal for adjusting the positioning of the adjustably positioned member in a direction to minimize the error signal.

37. The combination set forth in claim 36 wherein the control means includes a plug member defining a passage and further includes resilient means disposed in the passage to control the size of the passaage in accordance with the constraint of the resilient means and operatively coupled to the adjustably positioned member to become constrained in accordance with adjustments in the positioning of the member.

38. The combination set forth in claim 37 wherein the adjusting means includes a drive member coupled to the adjustably positioned means and further includes a motor operatively coupled to the drive member and responsive to the error signal for driving the drive member in a direction to minimize the error signal.

39. The combination set forth in claim 1 wherein the means defining the inlet and outlet lines and the passage and the adjustably positioned means are disposed in a cassette and the cassette includes the passage for receiving fluid from the inlet line and passing fluid to the outlet line and the error signal means include transducer means for sensing the rate of flow of fluid through the passage.

40. The combination set forth in claim 39 wherein resilient means are disposed in the cassette to define the passage and wherein the adjustably positioned member constrains the resilient means to control the size of the passage and wherein means are responsive to the signals from the transducer means for adjusting the constraint of the adjustably positioned means against the resilient means.

41. The combination set forth in claim 6 wherein the channel in the button is substantially V-shaped.

42. The combination set forth in claim 13 wherein the channel is substantially V-shaped.

43. The combination set forth in claim 32 wherein the adjustably positioned member is manually adjustable to control the rate of fluid flow and wherein the positioning means overrides the manual adjustment of the adjustably positioned means to adjust the positioning of the member to minimize the error signal.

44. In combination for controlling the rate of flow of fluid to a patient,
means for providing for a source of fluid,
means defining an inlet line from the source and an outlet line to the patient,
means disposed between the inlet line and the outlet line for defining a passage communicating with the inlet and outlet lines,
a button disposed in the passage in blocking relationship to the flow of fluid through the passage between the inlet and outlet lines,
there being at least one channel in the external surface of the button,
resilient means disposed in the passage at a position facing the button for controlling the size of the passage in accordance with the positioning of the resilient means in the passage relative to the button, and
adjustably positioned means disposed in coupled relationship to the resilient means for constraining the resilient means to control the size of the passage in accordance with adjustments in the positioning of the adjustably positioned means.

45. The combination set forth in claim 44 wherein the inlet and outlet lines are disposed on the same side of the passage and the resilient means faces the inlet and outlet lines.

46. The combination set forth in claim 45 wherein the channel is substantially V-shaped and the resilient means constitutes a diaphragm adjustably disposed in the V-shaped channel in accordance with constraints imposed upon the diaphragm.

47. The combination set forth in claim 46 wherein the fluid means, the inlet line, the outlet line, the passage, the button and the resilient means are disposed in a cassette and the adjustably positioned means extends from the cassette for manual adjustment.

48. In combination for controlling the flow of fluid from a source to a patient,
a housing,
an inlet line in the housing,
an outlet line in the housing,
a cavity in the housing in communication with the inlet and outlet lines,
a resilient diaphragm disposed in the cavity to define a particular boundary of a passage extending between the inlet and outlet lines,
means extending into the cavity from a position external to the housing and coupled to the diaphragm to constrain the diaphragm in accordance with the operation of the coupling means, and
a plurality of means disposed in the passage and cooperative with the diaphragm for controlling the flow of fluid through the passage between the inlet and outlet lines in accordance with the constraint of the diaphragm,
each of the means in the plurality being provided with parameters relative to the other means in the plurality to inhibit the flow of fluid through the passage with a different constraint of the diaphragm relative to the diaphragm constraint inhibiting the flow of fluid through the passage as a result of the operation of the other means in the plurality.

49. The combination set forth in claim 48 wherein the different means in the plurality are disposed at individual positions in the passage.

50. The combination set forth in claim 49 wherein the coupling means constitutes a rod extending into the housing from a position external to the housing and abutting the diaphragm to constrain the diaphragm in accordance with the movements of the rod.

51. The combination set forth in claim 50 wherein each of the means in the plurality defines a channel providing a communication through the passage between the inlet and outlet lines and wherein the diaphragm is positioned to close each of the channels in accordance with the constraint on the diaphragm.

52. The combination set forth in claim 51 wherein each of the channels in the plurality has an area different from the areas of the other channels in the plurality to provide for the closing of the different channels in accordance with progressive constraints of the diaphragm.

* * * * *